United States Patent [19]

Suzuki et al.

[11] 4,293,504

[45] Oct. 6, 1981

[54] PROCESS FOR PREPARING OPTICALLY ACTIVE α-CYANO-3-(4-HALOGENOPHENOXY)-BENZYL 2-(4-CHLOROPHENYL)ISOVALERATE

[75] Inventors: Yukio Suzuki, Toyonaka; Kiyoshi Kasamatsu, Takarazuka; Kohichi Aketa, Kawanishi, all of Japan

[73] Assignee: Sumitomo Chemical Company, Limited, Osaka, Japan

[21] Appl. No.: 118,716

[22] Filed: Feb. 5, 1980

[30] Foreign Application Priority Data

Feb. 5, 1979 [JP] Japan .................................. 54-12500

[51] Int. Cl.$^3$ ............................................ C07C 121/75
[52] U.S. Cl. ................................ 260/465 D; 424/304
[58] Field of Search ..................... 260/465 D; 424/304

[56] References Cited

U.S. PATENT DOCUMENTS 4,133,826  1/1979  Warnant et al. ................ 260/465 D

FOREIGN PATENT DOCUMENTS

| 853411 | 10/1977 | Belgium . |
| 857859 | 12/1977 | Belgium . |
| 2289 | 6/1979 | European Pat. Off. . |
| 7806273 | 12/1978 | Netherlands . |
| 7807368 | 1/1979 | Netherlands . |
| 2001964 | 2/1979 | United Kingdom . |
| 2014137 | 8/1979 | United Kingdom . |

*Primary Examiner*—Dolph H. Torrence
*Attorney, Agent, or Firm*—Sughrue, Mion, Zinn, Macpeak and Seas

[57] ABSTRACT

An optically active α-cyano-3-(4-halogenophenoxy)-benzyl 2-(4-chlorophenyl)isovalerate, which consists substantially of or is rich in (S)-α-cyano-3-(4-halogenophenoxy)benzyl (S)-2-(4-chlorophenyl)isovalerate; a method for preparing the same; and an insecticidal and/or acaricidal composition containing the same.

9 Claims, No Drawings

PROCESS FOR PREPARING OPTICALLY ACTIVE α-CYANO-3-(4-HALOGENOPHENOXY)-BENZYL 2-(4-CHLOROPHENYL)ISOVALERATE

BACKGROUND OF THE INVENTION

1. Field of the Invention

This invention relates to an optically active α-cyano-3-(4-halogenophenoxy)benzyl 2-(4-chlorophenyl)-isovalerate of the formula (I):

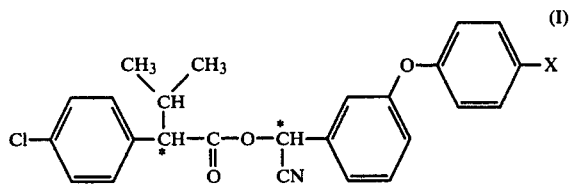

wherein X is a fluorine atom, a chlorine atom or a bromine atom, and * indicates an asymmetric carbon atom, which contains at least 60% of a compound of said formula having an (S)-configuration on both the acid and alcohol moieties; (S)-α-cyano-3-(4-halogenophenoxy)benzyl (S)-2-(4-chlorophenyl)isovalerate; a process for preparing the same; and an insecticide and/or acaricide containing the same.

2. Description of the Prior Art

α-Cyano-3-(4-halogenophenoxy)benzyl 2-(4-chlorophenyl)isovalerates are useful as insecticides and/or acaricides. These esters have one asymmetric carbon atom on each of the acid and alcohol moieties. An ester provided by the conventional method is a mixture comprising substantially equal amounts of four isomers.

These optical isomers are hereunder referred to as shown in Table 1 below.

TABLE 1

| | Abbreviations for Optical Isomers | | |
| | Acid Moiety | | |
| Alcohol Moiety | (S)-Configuration | Racemic | (R)-Configuration |
|---|---|---|---|
| (S)-Configuration | Aα-Isomer | α-Isomer | Bα-Isomer |
| Racemic | A-Isomer | "Racemate" | B-Isomer |
| (R)-Configuration | Aβ-Isomer | β-Isomer | Bβ-Isomer |

However, no single optical isomer which is optically active on both the acid and alcohol moieties has yet been synthesized, and as a matter of course, the relationship between the physiological activity and configuration has not been known.

SUMMARY OF THE INVENTION

As a result of syntheses of these optical isomers and review of the physiological activity thereof, the inventors have found that the Aα-isomer, i.e., an ester of the formula (I) having an (S)-configuration on both the acid and alcohol moieties has strong insecticidal and/or acaricidal activity and they have found an economical process for preparing the same, such leading to the accomplishment of this invention.

In addition, an Aα-isomer of a compound of the formula (I) wherein X is a fluorine atom (hereinafter, this compound being referred to as "p-fluoroester") has a stronger activity than other halogen-substituted compounds, and therefore, it is more important from an economical standpoint.

Of the optical isomers of the esters of the formula (I), the Aα-isomer has the strongest insecticidal and/or acaricidal efficacy which is on the order of about four times greater than that of "racemate" prepared by the conventional method. This fact was first revealed by the inventors and it is very important to understand the fact in controlling various harmful insects and/or mites.

This invention also provides an ester of the formula (I) having an (S)-configuration on the acid moiety, which is rich in the Aα-isomer. The biological activity of this ester generally increases in proportion to the content of the Aα-isomer. Such ester has economic advantages over a substantially pure Aα-isomer.

DETAILED DESCRIPTION OF THE INVENTION

One method of producing the Aα-isomer is by chromatography of a carboxylic ester of the formula (I) having an (S)-configuration on the acid moiety.

An α-cyano-3-(4-halogenophenoxy)benzyl 2-(4-chlorophenyl)isovalerate of the formula (I) having an (S)-configuration on the acid moiety is prepared by esterifying S-(+)-2-(4-chlorophenyl)isovaleric acid by a known method. The optically active carboxylic acid can be prepared by reacting the carboxylic acid in the racemic form with an optically active amine, followed by optical resolution of the reaction product (see Japanese Patent Application (OPI) No. 25544/75 (the term "OPI" as used herein refers to a "published unexamined Japanese patent application")).

The Aα-isomer may also be prepared via the following route (see K. Aketa et al., Agric. Biol. Chem., 42 (4), 895–896 (1978)):

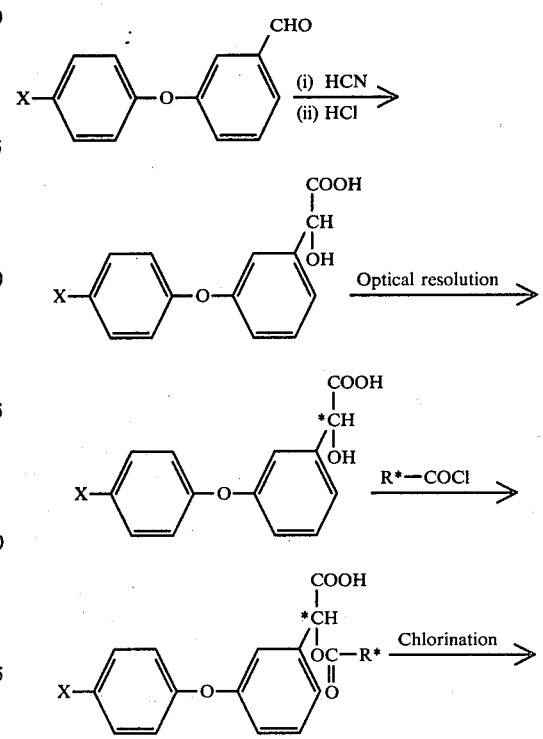

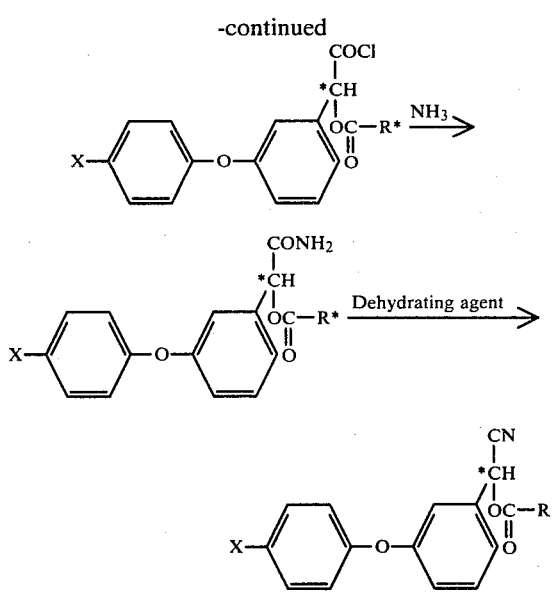

(wherein X has the same meaning as defined above; R* is a group represented by the formula

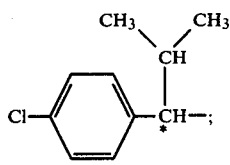

and * indicates an asymmetric carbon atom). However, these conventional methods are complicated and are not always suitable on an industrial scale.

With respect to α-cyano-3-phenoxybenzyl 2-(4-chlorophenyl)isovalerate, if a compound having an (S)-configuration on the acid moiety (A-isomer) is obtained, it is easy to form the Aα-isomer by selective crystallization. In this case, if the selective crystallization is carried out in the presence of a base, then the A-isomer can be converted to the Aα-isomer almost quantitatively (see U.S. patent application Ser. No. 922,476, filed July 7, 1978, and British patent application (OPI) No. 2,014,137). However, with respect to esters such as those in the present invention in which the alcohol moiety is constituted by an α-cyano-3-(4-halogenophenoxy)benzyl alcohol, such has not yet been known.

Therefore, the inventors continued to extensively study processes for preparing optically active esters of the formula (I) and found that the Aα-isomer can be crystallized. The inventors further found that the Aα-isomer crystal can be selectively crystallized from a solution of the corresponding ester of the formula (I) having an (S)-configuration on the acid moiety and that the presence of a basic catalyst in the crystallization system helps increase the yield of the Aα-isomer crystal greatly. Based on these findings, the inventors have established a process for producing the optically active ester of this invention very advantageously on an industrial scale.

The process comprises crystallizing an Aα-isomer from a solution of an ester of the formula (I) having an (S)-configuration on the acid moiety in the presence or absence of a basic catalyst, followed by separation of the crystal from the mother liquor.

If crystallization and separation of the crystal are effected in the absence of a basic catalyst, the ester recovered from the mother liquor contains an increased amount of the Aβ-isomer is brought into contact with a basic catalyst to epimerize it on the alcohol moiety. After the ratio of the Aα-isomer to the Aβ-isomer reaches equilibrium, the crystallization is further conducted whereby the ester of the formula (I) having an (S)-configuration on the acid moiety can be converted to the Aα-isomer almost quantitatively. If crystallization and separation of the crystal are effected in the presence of a basic catalyst, it becomes possible to obtain the crystal of the Aα-isomer in an amount higher than that initially contained (usually in an amount of about 50%) in the starting ester of the formula (I) having an (S)-configuration on the acid moiety. In this case, the ester remaining in the mother liquor may be recovered and purified for use as the starting material for the next crystallization.

Alternatively, the crystal of the Aα-isomer is crystallized from the ester of the formula (I) having an (S)-configuration on the acid moiety in the presence of a basic catalyst, the basic catalyst is removed or inactivated (or neutralized) without separating the crystal from the mother liquor, and the whole is then subjected to concentration or the like to recover the ester of the formula (I) having an (S)-configuration on the acid moiety together with the crystal of the Aα-isomer whereby the ester having an (S)-configuration on the acid moiety which is rich in the Aα-isomer becomes available.

This alternative method is more advantageous from the industrial and economical standpoints because it permits effective use of the Aα-isomer remaining in the mother liquor without losing it and is a simpler operation.

In any of the methods described above, it is preferred that the starting ester of the formula (I) having an (S)-configuration on the acid moiety desirably is in the racemic form on the alcohol moiety, but in the presence of a basic catalyst, any proportion of the (S)-configuration to the (R)-configuration on the alcohol moiety may be used. It is preferred that the optical purity on the acid moiety is 80% or more, preferably 90% or more.

It is to be emphasized that the ester of the formula (I) having an (S)-configuration on the acid moiety which is rich in the Aα-isomer may be recrystallized to provide the Aα-isomer of higher purity.

In the process of this invention, since the ester used as the starting material is a liquid which is hardly fluid at the crystallization temperature, a solvent is generally used. Any solvent may be used without particular limitation so long as it dissolves therein the A-isomer or the Aβ-isomer to a moderate extent and has a sufficiently low solubility to the Aα-isomer. Examples of the solvent are aliphatic hydrocarbons, e.g., hexane, heptane, etc., alicyclic hydrocarbons, e.g., methylcyclohexane, etc., lower alcohols, e.g., methanol, ethanol, etc., and mixed solvents containing the same. Of these, the lower alcohols are preferred with methanol being particularly preferred. The concentration of the starting ester in the solution can be freely selected from the range of 1 to 95 wt%, preferably 20 to 80 wt%.

Crystallization of the Aα-isomer is preferably performed by seeding with crystals. Examples of the seed crystals are the crystal of the Aα-isomer or Bβ-isomer of the corresponding ester, a mixture comprising equal amounts of these two crystals and a mixture of any proportion of these crystals. There is no particular limitation on the amount of the seed crystals used, and the use of a high amount of seed crystals generally results in rendering the more efficient crystallization. The crystallization of the Aα-isomer can be carried out continuously or semicontinuously. In this case, the seeding with crystals may be effected only at the initiation of crystallization of the Aα-isomer.

Examples of the basic catalyst include nitrogen-containing bases such as ammonia, hydrazine, methylamine, ethylamine, n-propylamine, isopropylamine, n-butylamine, dimethylamine, diethylamine, di-n-propylamine, di-n-butylamine, trimethylamine, triethylamine, cyclohexylamine, ethylenediamine, ethanolamine, pyrrolidine, piperidine, morpholine, aniline, 1-naphthylamine, pyridine, quinoline, 1,5-diazabicyclo[4,3,0]-none-5-ene, etc., phosphorus-containing bases such as triphenylphosphine, tri-n-butylphosphine, etc., quaternary ammonium hydroxides such as tetramethylammonium hydroxide, tetra-n-butylammonium hydroxide, etc., metal-containing bases such as sodium hydroxide, potassium hydroxide, sodium carbonate, sodium cyanide, sodium methylate, sodium hydride, sodium amide, talc, bentonite, etc., basic ion exchange resins, and the like, with the ammonia and triethylamine being preferred.

The proportion of the catalyst to the starting ester may be freely selected from the range of from 0.001 mol% to 100 mol%, preferably from 1 mol% to 100 mol%, if the catalyst is a weak base such as nitrogen-containing and phosphorus-containing bases, etc. Strong bases such as quaternary ammonium hydroxide, sodium hydroxide, potassium hydroxide, sodium hydride, etc., are desirably used in an amount not greater than 10 mol% to prevent significant decomposition of the catalyst.

Theoretically, a crystallization temperature lower than the melting point of the desired Aα-isomer may be used, but the process of this invention is generally performed at a temperature lower than the melting point by about 20° C. and preferably at $-50°$ C. to 0° C.

The α-isomer or β-isomer can be synthesized by reacting optically active 3-(4-halogenophenoxy)mandelic acid with (R,S)-2-(4-chlorophenyl)isovaleryl chloride in accordance with the method taught in K. Aketa et al., *Agric. Biol. Chem.*, 42 (4), 895–896 (1978) described above.

The compound and the process for preparing the same according to this invention are hereunder described in greater detail by reference to the following examples which are given here for illustrative purposes only and are by no means intended to limit the invention.

In the examples, the ratio of the Aα-isomer to the Aβ-isomer was analyzed by gas chromatography.

EXAMPLE 1

To 8.65 g (40 mmol) of 3-(4-fluorophenyloxy)-benzaldehyde were added 9.50 g (41 mmol) of S-(+)-2-(4-chlorophenyl)isovaleryl chloride and then 30 cc of n-hexane, and the mixture was stirred in a nitrogen atmosphere. Separately, 2.48 g (95% grade, 48 mmol) of sodium cyanide and 80 mg of benzyl triethyl ammonium chloride were dissolved in 20 cc of water, and the solution was dropwise added to the mixture at 20° to 25° C. over a period of 30 minutes, followed by stirring the resulting mixture for 7 hours. The aqueous layer was separated, and 10 cc of toluene was added to the oily layer which was then washed twice with water. The oily layer was concentrated under reduced pressure to give 16.99 g (yield based on the aldehyde: 97.0%) of an A-isomer of a p-fluoroester (of the formula (I) wherein X is a fluorine atom) as a yellow viscous oily matter.

$n_D^{22.5°} = 1.5602$, $[\alpha]_D^{23°} = -7.7°$ (in chloroform, C=4.9 g/dl)

EXAMPLE 2

The procedure of Example 1 was repeated except that the S-(+)-2-(4-chlorophenyl)isovaleryl chloride was replaced by R-(−)-2-(4-chlorophenyl)isovaleryl chloride to obtain a B-isomer of the p-fluoroester. (yield: 97.5%)

$n_D^{22.5°} = 1.5621$, $[\alpha]_D^{23°} = +8.4°$ (in chloroform, C=2.0 g/dl)

EXAMPLE 3

The same procedure of Example 1 was repeated except that the 3-(4-fluorophenyloxy)benzaldehyde was replaced by 3-(4-chlorophenyloxy)benzaldehyde to obtain an A-isomer of a p-chloroester (of the formula (I) wherein X is a chlorine atom). (yield: 98.4%)

$n_D^{22.5°} = 1.5739$, $[\alpha]_D^{23°} = -8.4°$ (in chloroform, C=3.9 g/dl)

EXAMPLE 4

The same procedure of Example 1 was repeated except that the 3-(4-fluorophenyloxy)benzaldehyde was replaced by 3-(4-bromophenyloxy)benzaldehyde to obtain an A-isomer of a p-bromoester (of the formula (I) wherein X is a bromine atom). (yield: 99.8%)

$n_D^{22.5°} = 1.5828$, $[\alpha]_D^{22°} = -9.9°$ (in chloroform, C=2.3 g/dl)

EXAMPLE 5

700 mg of the A-isomer of the p-fluoroester prepared in Example 1 was dissolved in hexane, and the solution was adsorbed on a silica gel column (Lobar Column, Size B Lichroprep Si 60; a product of Merck Co.) and eluted with a mixed solvent of hexane and ethyl acetate (80:1). The eluate was subjected to gas chromatography to determine the ratio of the Aβ-isomer to the Aα-isomer. Fractions (Aα-isomer) which were eluted later during the gas chromatograph were combined and concentrated to obtain 156 mg of the Aα-isomer.

m.p.: 40.0°–43.2° C., $[\alpha]_D^{23°} = -10.7°$ (in chloforom, C=3.1 g/dl)

EXAMPLE 6

The procedure of Example 5 was repeated to separate the Aα-isomer of the p-chloroester from the A-isomer of the p-chloroester prepared in Example 3.

m.p.: 61°–64° C., $[\alpha]_D^{22°} = -9.5°$ (in chloforom, C=3.2 g/dl)

EXAMPLE 7

The procedure of Example 5 was repeated to separate the Aα-isomer of the p-bromoester from the A-isomer of the p-bromoester prepared in Example 4.

m.p.: 71.0°–73.1° C., $[\alpha]_D^{23°} = -7.5°$ (in chloroform, C=0.93 g/dl)

EXAMPLE 8

5 g of the A-isomer of the p-fluoroester prepared in Example 1 was dissolved in 10 g of methanol, and the solution was cooled to $-15°$ C. A mixture of 1 mg of, as a seed crystal, the Aα-isomer and 0.2 cc of a 10.5% ammonia-methanol solution was added to the solution, and the resulting mixture was stirred at $-15°$ C. for a day. The crystal was collected by filtration, washed with a small amount of cold methanol ($-25°$ to $-10°$ C.), and dried in vacuo to obtain 3.52 g of the crystal of Aα-isomer. (yield: 70.4%).

m.p.: 40.6°–43.5° C. $[α]_D^{24°} = -10.5°$ (in chloroform, C=2.5 g/dl)

EXAMPLE 9

6.09 g of the A-isomer of the p-bromoester prepared in Example 4 was dissolved in 12.2 g of methanol, and the solution was cooled to $-6°$ C. A mixture of 0.2 cc of a 10.5% ammonia-methanol solution and 1 mg of, as a seed crystal, the Aα-isomer was added to the solution, and the resulting mixture was stirred at $-6°$ C. One day later, the crystal was collected by filtration, washed with cold methanol ($-15°$ to $-5°$ C.) and vacuum-dried to provide 4.67 g (yield: 76.7%) of the Aα-isomer.

m.p.: 71.0°–73.0° C., $[α]_D^{24°} = -7.8°$ (in chloroform, C=3.0 g/dl)

EXAMPLE 10

5 g of the A-isomer of the p-chloroester prepared in Example 3 was dissolved in 12.2 g of methanol, and the solution was cooled to $-15°$ C. A mixture of 0.2 cc of a 10.5% ammonia-methanol solution and 1 mg of, as a seed crystal, the Aα-isomer was added to the solution, and the resulting mixture was stirred at $-15°$ C. One day later, 20 cc of toluene and 20 cc of a 1% aqueous hydrochloric acid were added to the reaction system, and the resulting mixture was thoroughly stirred at 20° to 25° C. The aqueous layer was separated, and the oily layer was thoroughly washed with water and concentrated under reduced pressure to provide 4.81 g of the A-isomer containing 85% of the Aα-isomer.

$n_D^{22°} = 1.5498$, $[α]_D^{23°} = -9.0°$ (in chloroform, C=1.9 g/dl)

The insecticides and/or acaricides of this invention are highly effective in controlling the below illustrated harmful insects on field crops, fruit trees, vegetables, forests and woodwork, insanitary insects and harmful insects on livestock, exhibit a high insecticidal and/or acaricidal activity and residual activity against these harmful insects, and have low toxicity to mice, rats and other mammals. For this reason, there is no particular limitation on the field where the compound of this invention can be used with advantage.

1. Order Hemiptera:

white-backed planthopper, smaller brown planthopper, brown planthopper, green rice leafhopper, grain aphid, green peach aphid, cotton aphid, cabbage aphid, common green stink bug, azalea lacewing bug, citrus phitefly 2. Order Lepidoptera:

peach leaf miner, tea leaf roller, apple leaf miner, citrus leaf miner, diamond-back moth, summer fruit tortrix, tea tortrix, rice stem borer, grass leaf roller, corn borer, pine moth, tent caterpillar, akebia leaf-like moth, armyworm, cabbage armyworm, tobacco cutworm, smaller citrus dog 3. Order Coleoptera:

striped flea beetle, daikon leaf beetle, rice leaf beetle, rice plant weevil, azuki bean weevil, cupreous chafer, soybean beetle 4. Order Diptera:

yellow fever mosquito, anopheles, common mosquito, housefly, onion maggot, green bottle fly, flesh fly, rice leaf miner 5. Order Orthoptera:

short-winged rice grasshopper

6. Order Isoptera:

Formosan subterranean termite, Japanese termite

7. Order Blattoidea:

German cockroach, American cockroach, smoky brown cockroach

8. Order Acarina:

carmine mite, two-spotted spider mite, sugi spider mite, citrus red mite, European red mite, Japanese citrus rust mite, cyclamen mite, cattle tick The compound of this invention may be applied to the field without being combined with other ingredients, but it is more common to make a formulation using a carrier that facilitates handling as a controlling agent and to use the formulation after suitable dilution. Any desired formulation such as an emulsifiable concentrate, a wettable powder, a dust, a granule, a fine granule, an oil, an aerosol, a thermal fumigant (e.g., mosquito coil, an electric mosquito repellent, etc.), a spray such as fogging, a non-thermal fumigant, and poisonous bait may be made of the compound of this invention without requiring a special condition and in accordance with the method familiar to the skilled in the art of manufacture of general agrichemicals. The formulations prepared may be used in various applications depending on the purpose.

Two or more compounds of this invention may be combined to exhibit a higher insecticidal and/or acaricidal activity. The insecticidal and/or acaricidal activity of the compound of the invention may also be enhanced by mixing it with known synergists for pyrethroids, such as α-[2-(2-butoxyethoxy)ethoxy]-4,5-methylenedioxy-2-propyltoluene (hereinafter referred to as piperonylbutoxide (PBO)), 1,2-methylenedioxy-4-[2-(octylsulfinyl)propyl]-benzene (hereinafter referred to as sulfoxide), 4-(3,4-methylenedioxyphenyl)-5-methyl-1,3-dioxane (hereafter referred to as safroxane), N-(2-ethylhexyl)bicyclo[2,2,1]-hepta-5-ene-2,3-dicarboximide (hereinafter referred to as MGK-264), octachlorodipropyl ether (referred to as S-421), isobronyl thiocyanoacetate (hereinafter referred to as thanite), etc., and known effective synergists for allethrin and pyrethrin.

While the compound of this invention is stable against light, heat and oxidation, a stabler compound may be made by incorporating therein a suitable amount of an antioxidant, a UV absorber, or a stabilizer such as a phenol derivative, e.g., BHT or BHA, a bisphenol derivative, arylamines such as phenyl-α-naphthylamine, phenyl-β-naphthylamine, and a condensate of phenetidine and acetone, or a benzophenone compound.

Multipurpose compositions may be prepared or synergistic effect may be provided by combining the compound of this invention with other physiologically active substances such as allethrin, N-(chrysanthemoylmethyl)-3,4,5,6-tetrahydrophthalimide (hereinafter referred to as tetramethrin), 5-benzyl-3-furylmethyl chrysanthemate (hereinafter referred to as resmethrin), 3-phenoxybenzyl chrysanthemate, 5-propargylfurfuryl chrysanthemate, and other known cyclopropane carboxylic esters and isomers thereof or pyrethrum extract, organophosphorus insecticides and acaricides such as O,O-dimethyl O-(3-methyl-4-nitrophenyl)phosphorothioate (hereinafter referred to as fenitrothion), O,O- dimethyl O-4-cyanophenylphosphorothioate (hereinafter referred to as cyanophos) and O,O-dimethyl O-(2,2-dichlorovinyl)phosphate (hereinafter referred to as dichlorovos), carbamate insecticides such as 1-naphthyl N-methylcarbamate, 3,4-dimethylphenyl N-methylcarbamate, meta-tolyl N-methylcarbamate, O-sec-butylphenyl N-methylcarbamate, O-isopropoxyphenyl N-methylcarbamate, 3-methyl-4-dimethylaminophenyl N-monomethylcarbamate and 4-dimethylamino 3,5-xylylmethylcarbamate, and other insecticides, acaricides, fungicides, nematocides, herbicides, plant growth regulators, fertilizers, pesticides against microorganism, insect hormones and other pesticides.

The compound of this invention may be incorporated in an insecticidal and/or acaricidal composition in an amount which preferably ranges from 0.001% to 80%, more preferably from 0.01% to 50%.

The high insecticidal and/or acaricidal efficacy of the compound of this invention is hereinafter described in detail by the following illustrative formulation examples and test examples.

| Compound No. of this Invention | Structure ["X" in the formula (I)] | Isomer | Example No. |
|---|---|---|---|
| (1) | X: F | A-Isomer | 1 |
| (2) | | Aα-Isomer | 5 |
| (3) | X: Cl | Aα-Isomer | 6 |
| (4) | X: Br | A-Isomer | 4 |
| (5) | | Aα-Isomer | 7 |

FORMULATION EXAMPLE 1

10 parts of each of the compounds of this invention, (1), (2), (3), (4) and (5) was mixed with 15 parts of Sorpol 3005x (a registered trademark of Toho Chemical Co., Ltd.) and 75 parts of xylene, and the mixture was thoroughly stirred to provide a 10% emulsifiable concentrate.

FORMULATION EXAMPLE 2

0.5 part of each of the compounds of this invention, (1), (2), (3), (4) and (5) was dissolved in 20 parts of acetone. To the solution was added 99.5 parts of 300 mesh clay, and the mixture was thoroughly stirred. The acetone was distilled off to provide a 0.5% dust.

FORMULATION EXAMPLE 3

0.2 part of each of the compounds of this invention, (1), (2), (3), (4) and (5) was mixed with 2 parts of m-tolyl N-methylcarbamate and 0.3 part of PAP (isopropyl acid phosphate), and the mixture was dissolved in 20 parts of acetone. To the solution was added 97.5 parts of 300 mesh clay, and the mixture was stirred thoroughly. The acetone was distilled off to provide a 2.2% dust.

FORMULATION EXAMPLE 4

50 parts of each of the compounds of this invention, (1), (2), (3), (4) and (5) was thoroughly mixed with Sorpol 5029-0 (special anionic surfactant). To the mixture was added 45 parts of 300 mesh diatomaceous earth, and the resulting mixture was thoroughly stirred to provide a 50% wettable powder.

FORMULATION EXAMPLE 5

10 parts of each of the compounds of this invention (1), (2), (3), (4) and (5) was mixed with 2.0 parts of dimethyl S-methylcarbamoylmethyl phosphorothionate. To the mixture were added 5 parts of Sorpol 3005x (described above) and 80 parts of 300 mesh diatomaceous earth. The resulting mixture was thoroughly stirred to provide a 30% wettable powder.

FORMULATION EXAMPLE 6

2 parts of each of the compounds of this invention, (1), (2), (3), (4) and (5) was thoroughly mixed with 2 parts of sodium lignin sulfonate (binder) and 96 parts of clay (carrier) in a triturator. Water was added to the mixture with stirring in an amount of 10 wt% based on the mixture. The resulting mixture was passed through a granulator to form granules which were then air-dried to provide a 2% granule.

FORMULATION EXAMPLE 7

0.5 part of the compound (1) of this invention was dissolved in illuminating kerosine to make a total of 100 parts to provide a 0.5% oil.

FORMULATION EXAMPLE 8

A mixture of 0.5 part of the compound (2) of this invention and 2 parts of PBO (described above) was dissolved in illuminating kerosine to make a total of 100 parts to provide a 0.5% oil.

It will be demonstrated by the following test examples that the thus formulated insecticides and acaricides of this invention exhibit a high efficacy.

In the following test examples, the "racemate" (conventional product) of each of the compounds of the formula (I) was formulated in the same procedures as in each test example and then used as a reference compound.

Reference Compound
(a): a compound of the formula (I) wherein X=F
(b): a compound of the formula (I) wherein X=Cl
(c): a compound of the formula (I) wherein X=Br

TEST EXAMPLE 1

Each of the emulsifiable concentrates prepared from the compounds of this invention, (1), (2), (3), (4) and (5) in the procedures described in Formulation Example 1 was diluted with water to a predetermined concentration, and a sticker containing 20% of an alkylphenol polyethylene glycol ether and 12% of a salt of lignin sulfonic acid was added to the solution in an amount of 1 ml per 3,000 ml of the solution. Leaves of cabbage 2 months old after seeding were immersed in each solution for 1 minute. Ten 3rd-instar larvae of tobacco cutworm were further immersed in each solution for 10 seconds. The leaves and cutworms were air-dried and placed in each plastic cup having a diameter of 10 cm and a height of 4 cm. 48 hours later, the alive and dead was evaluated to obtain the $LC_{50}$ (median lethal concentration) (ppm).

| Compound | $LC_{50}$ (ppm) | Relative Efficacy (reference compound: 100) |
|---|---|---|
| Compound (1) | 2.3 | 217 |
| Compound (2) | 1.2 | 417 |
| Reference Compound (a) | 5.0 | 100 |
| Compound (3) | 3.9 | 390 |

-continued

| Compound | LC$_{50}$ (ppm) | Relative Efficacy (reference compound: 100) |
|---|---|---|
| Reference Compound (b) | 15.2 | 100 |
| Compound (4) | 9.5 | 211 |
| Compound (5) | 4.2 | 476 |
| Reference Compound (c) | 20.0 | 100 |

TEST EXAMPLE 2

The compounds of this invention, (1), (2), (3), (4) and (5) were diluted with acetone to a predetermined concentration, and 0.5 μl of each solution was topically applied to thorax of female adult CSMA-strain houseflies with a microsyringe. The flies were placed in a plastic cup having a diameter of 12 cm containing therein cotton absorbent impregnated with 3% sugar water. 24 hours later, the alive and dead was evaluated to determine the LD$_{50}$ (median lethal dose) (μg/insect).

| Compound | LD$_{50}$ (μg/insect) | Relative Efficacy (reference compound: 100) |
|---|---|---|
| Compound (1) | 0.019 | 216 |
| Compound (2) | 0.010 | 410 |
| Reference Compound (a) | 0.041 | 100 |
| Compound (3) | 0.016 | 388 |
| Reference Compound (b) | 0.062 | 100 |
| Compound (4) | 0.035 | 229 |
| Compound (5) | 0.018 | 444 |
| Reference Compound (c) | 0.080 | 100 |

TEST EXAMPLE 3

The dusts prepared from the compounds of this invention, (1), (2), (3), (4) and (5) in the procedures described in Formulation Example 2 were applied to rice seedlings planted in each 3 inch pot and 20 days old after seeding. A bell-jar duster was used to apply each dust at a pressure of 200 mmHg at a rate of 2 kg/10 ares. After the treatment, each pot was enclosed with a metal screen cage in which about 30 adult green rice leafhoppers were released. 24 hours later, the alive and dead was evaluated to found that the leafhoppers were completely killed.

TEST EXAMPLE 4

10 to 15 female adult carmine mites were placed on each leaf of potted kidney beans (2-leaf stage) 9 days old after seeding. After standing in a constant temperature room at 27° C. for a week, a lot of mites in various growth stages were observed on the beans. Each of the emulsifiable concentrates prepared from the compounds of this invention (1) and (2) in the procedures described in Formulation Example 1 was diluted 500-fold with water and applied to the beans on a turntable at a rate of 10 ml/pot. Observation 10 days later showed the mite-released kidney beans were little damaged.

While the invention has been described in detail and with reference to specific embodiments thereof, it will be apparent to one skilled in the art that various changes and modifications can be made therein without departing from the spirit and scope thereof.

What is claimed is:

1. A process for preparing the compound (S)-α-cyano-3-(4-halogenophenoxy)benzyl (S)-2-(4-chlorophenyl)isovalerate, substantially free of other isomers, which comprises crystallizing said compound from a solution of the compound of the formula

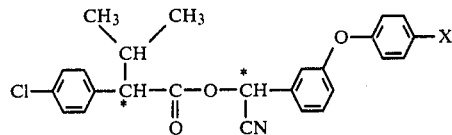

wherein X is a fluorine atom, a chlorine atom or a bromine atom, and * indicates an asymmetric carbon atom, having an (S)-configuration on the acid moiety with or without being seeded with crystals in the presence or absence of a basic catalyst, and separating the crystal of said compound from the mother liquor.

2. The process according to claim 1, wherein the crystallization is carried out in the presence of a basic catalyst.

3. A process for preparing an optically active α-cyano-3-(4-halogenophenoxy)benzyl 2-(4-chlorophenyl)isovalerate of the formula

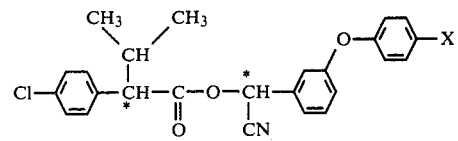

wherein X is a fluorine atom, a chlorine atom or a bromine atom, and * indicates an asymmetric carbon atom, which consists of at least 60% of (S)-α-cyano-3-(4-halogenophenoxy)benzyl (S)-2-(4-chlorophenyl)isovalerate, which comprises crystallizing said compound from a solution of the compound of said formula having an (S)-configuration on the acid moiety with or without being seeded with crystals in the presence of a basic catalyst, and recovering the crystal of said compound together with the compound of said formula having an (S)-configuration on the acid moiety contained in the mother liquor.

4. The process according to claims 1 or 3, wherein said basic catalyst is a nitrogen-containing base.

5. The process according to claim 4, wherein said nitrogen-containing base is ammonia or triethylamine.

6. The process according to claims 1 or 3, wherein a solvent selected from the group consisting of a lower alcohol, an aliphatic hydrocarbon, an alicyclic hydrocarbon, a mixture thereof, and a solvent containing at least one of these solvents is used as a solvent for the crystallization.

7. The process according to claim 6, wherein said lower alcohol is methanol.

8. The process according to claims 1 or 3, wherein the process is characterized by seeding with crystals.

9. The process according to claims 1 or 3, wherein the crystallization is carried out continuously or semicontinuously.

* * * * *